(12) United States Patent
Beling et al.

(10) Patent No.: US 9,327,106 B2
(45) Date of Patent: May 3, 2016

(54) PORTAL AND SEPTUM THEREFOR

(71) Applicant: SMITHS MEDICAL ASD, INC., Rockland, MA (US)

(72) Inventors: William Lloyd Beling, New Brighton, MN (US); Kristin Finberg, Minneapolis, MN (US); Ronald Gene Travis, Spring Lake Park, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 5 days.

(21) Appl. No.: 14/205,448

(22) Filed: Mar. 12, 2014

(65) Prior Publication Data

US 2014/0276473 A1    Sep. 18, 2014

Related U.S. Application Data

(60) Provisional application No. 61/781,210, filed on Mar. 14, 2013.

(51) Int. Cl.
*A61M 37/00* (2006.01)
*A61M 31/00* (2006.01)
*A61M 39/02* (2006.01)

(52) U.S. Cl.
CPC ... *A61M 39/0208* (2013.01); *A61M 2039/0238* (2013.01)

(58) Field of Classification Search
USPC ............................. 604/116, 288.01–288.04
See application file for complete search history.

(56) References Cited

U.S. PATENT DOCUMENTS

| 4,636,194 A | 1/1987 | Schulte |
|---|---|---|
| 5,662,600 A | 9/1997 | Watson |

(Continued)

FOREIGN PATENT DOCUMENTS

| EP | 0 239 244 | 9/1987 |
|---|---|---|
| WO | WO 90/01958 | 3/1990 |
| WO | WO 95/15194 | 6/1995 |

OTHER PUBLICATIONS

PCT International Search Report (PCT/ISA/210); Written Opinion of the ISA/KR (PCT/ISA/237), re: PCT Application No. PCT/US2014/023867), mailed Aug. 6, 2014.

(Continued)

*Primary Examiner* — Theodore Stigell
*Assistant Examiner* — Tiffany Legette
(74) *Attorney, Agent, or Firm* — Louis Woo (57) ABSTRACT

An implantable portal includes a septum that has embedded therein a plurality of formations that together form an indicia adapted to identify at least one characteristic of the portal. The formations are configured from impressions formed on different layers of the septum spatially separated along the vertical axis of the septum. The impressions are filled with a radiopaque material. The superposed formations do not overlap when viewed from atop the septum. When viewed under radiographic imaging from the top of the septum, a 3-D identification indicia is presented to the viewer. The 3-D indicia may be used as a 3-D marker to focus the location of the septum where a needle to access the fluid reservoir of the portal may be inserted.

20 Claims, 7 Drawing Sheets

(56) References Cited

U.S. PATENT DOCUMENTS

| | | | |
|---|---|---|---|
| 5,931,829 | A | 8/1999 | Burbank et al. |
| 6,039,712 | A | 3/2000 | Fogarty et al. |
| 6,213,973 | B1 | 4/2001 | Elinsen et al. |
| 6,287,293 | B1 | 9/2001 | Jones et al. |
| 6,419,680 | B1 | 7/2002 | Cosman et al. |
| 2004/0106942 | A1 | 6/2004 | Taylor et al. |
| 2009/0227862 | A1 | 9/2009 | Smith et al. |
| 2009/0227951 | A1 | 9/2009 | Powers et al. |
| 2011/0092921 | A1* | 4/2011 | Beling et al. ............. 604/288.02 |
| 2011/0257609 | A1 | 10/2011 | Bizup et al. |
| 2011/0288503 | A1* | 11/2011 | Magalich et al. ........ 604/288.02 |
| 2012/0078202 | A1 | 3/2012 | Beling et al. |
| 2012/0226244 | A1 | 9/2012 | Beasley et al. |

OTHER PUBLICATIONS

Heischreiber, Klaus, of Medtron AG, Prüfzertifikat, Sep. 20, 2011.
Meywirth, M., Ref: VA 4-1, Development Test Report E-0717, Component Approval Portsysteme & NonCor Plus 19G x 20mm, Mar. 30, 2009, 18 pgs., Freseniun Kabi Deutschland GmbH.
Salis et al., "Maximal Flow Rates Possible during Power Injection through Currently Available PICCs: An In Vitro Study", JVIR Mar. 2004, vol. 15, No. 3, pp. 275-281.
Gebauer et al., "Contrast Media Power Injection Using Central Venous Port Catheters—Results of an In Virto Study", Fortschr Röntgenstr published Aug. 11, 2005; 177: pp. 1417-1423.
Intraport II Port-Kathetersystem aus Polyarylamid brochure catalog, Freseniun Kabi Deutschland GmbH, Art. Nr. 7315331/D4-04/04.
Intraport II by Freseniun Kabi, instructions for use.

* cited by examiner

PORTAL AND SEPTUM THEREFOR

FIELD OF THE INVENTION

The instant invention relates to implantable medical devices and more particularly to a portal having a 3-D identification indicia and/or marker embedded in the septum of the portal that can readily be seen under radiographic imaging.

BACKGROUND OF THE INVENTION

The portal of the instant invention is a subcutaneous implantable access device that includes a reservoir and a septum through which fluid may be input or removed from the reservoir. Such subcutaneous implantable device is known and is commonly referred to as a port or portal, and is exemplified by the following patents assigned to the assignee as the instant application: U.S. Pat. Nos. 5,558,641, 5,562,618, 5,613,945, 5,743,873 and 5,989,216. The respective disclosures of the '641, '618, '945, '873 and '216 patents are incorporated by reference to the disclosure of the instant application. Such portals are implanted into patients, with the self resealable septums of the portals providing access to the reservoirs so that fluid medicaments and other infusate fluids may be stored in the reservoirs for infusion to the patients. Instead of storing medication to be infused to the patient, patient fluid such as blood may be withdrawn from the reservoir, by using for example a cannula or needle.

For portals that have been implanted into patients, oftentimes it is necessary to determine given properties or characteristics of those portals, for example determining whether a certain portal is adaptable to be used for power injection. Accordingly, it is desirable that some indicia be provided to a portal so that even after the portal has been implanted into a patient, the particular characteristic(s) or property(s) of the portal can be ascertained.

There are a number of implantable portals that have an identifier that is discernable by x-ray or palpations. These portals are disclosed in US patent publication Nos. 2009/0024024, 2007/0276344, 2005/0124980, 2006/0224129 and 2008/0319399. The portals disclosed in the noted patent publications either have septums that have protuberances formed at its outer surface so that the portals may be palpated by the user over the skin of the patient, or have identifiers etched to the body of the portals that are x-ray viewable.

In U.S. Pat. No. 8,092,435, assigned to the same assignee as the instant application, the inventors of the instant application disclose a septum with an identification indicia embedded onto the top of the elastomer structure with a clear coat of silicone covering the identification indicia. The main purpose of the '435 invention is to provide an indicia that identifies a characteristic of the portal. The indicia is formed by an impression at the top surface of a base that is filled with a radiographic material and covered with the silicone layer. The disclosure of the '435 patent is incorporated by reference to the disclosure of the instant application.

BRIEF SUMMARY OF THE INVENTION

The instant invention portal improves on the portal disclosed in U.S. Pat. No. 8,092,435, and in particular increases the visibility of the portal by presenting a 3-D (3-dimensional) view of the identification indicia at the septum without having to rotate the imaging sensor(s) of the radiographic machine(s) relative to the portal when the portal is implanted in a patient. The instant invention provides the further advantage of presenting the identification indicia as a 3-D portal marker, at the septum, to the clinician viewer to readily guide him in inserting the needle into the reservoir chamber of the portal, to thereby eliminate the need for the clinician to guess or estimate the septum location to insert the needle.

The portal of the instant invention has a septum comprising an elastomeric silicone rubber structure. The septum includes a plurality of formations embedded therein. The formations are spatially separated within the septum along a first direction, for example the vertical axis of the septum as view from the top of the septum. The formations may be impressions formed at different layers of the septum that preferably correspond to planes that are in parallel and extend along a second direction orthogonal to the first direction, for example the horizontal axis of the septum. The different formations have respective configurations that do not overlap each other, when viewed from the top the septum along the first direction. When viewed along the first direction from the top of the septum, the plurality of formations provide a 3-D identification indicia and/or a 3-D marker to the viewer to inform him the portal type as well as the location at the portal where the needle may be inserted to gain access to the fluid reservoir inside the portal.

As the septum is preferably made from silicone, conventional silicone rubber molding processes such as transfer molding and LIM (liquid injection molding) may be used in the manufacturing of the septum structure. The impressions are formed to present selective outlines of configurations of an identification indicia and a marker during the molding process. The identification indicia may be adapted to convey information identifying a particular characteristic or property, or given characteristics or properties, of the portal. To enhance visibility, the impressions are filled with a radiopaque material such as for example barium sulfate ($BaSO_4$).

Each of the impression layers may be formed separately. After a molded impression is filled with the radiopaque material, liquid silicone is injected onto the top of the layer and another layer of impression is formed thereon at a predetermined distance. After all of the impression layers are formed and the respective impressions are filled with the radiopaque material, a liquid silicone may be injected onto the top surface. When solidified or hardened, the different layers of silicone become a one piece unitary integral septum that has embedded therein the different formations formed by the radiopaque material filled impressions. Due to the radiopaque material, when viewed from the top and along the vertical axis of the portal (the septum having fitted to the portal) by either x-ray or computer tomography imaging, the different layers of formations embedded in the septum would present a 3-D identification indicia and/or marker to the viewer.

The present invention is therefore directed to a self resealable septum that comprises: an elastomeric structure having at least two impressions embedded therein, the impressions being spatially separated from each other along one direction of the structure, each of the impressions configured to have a formation, the formations resulting from the impressions spatially separated from each other along the one direction to present a 3-D identification indicia to a viewer when the structure is viewed along the one direction under radiographic imaging.

The instant invention is further directed to subcutaneously implantable port, that comprises: a housing having an opening and an outlet; and a resealable elastomeric septum fitted to the opening of the housing to define a fluid reservoir inside the housing, the septum having a plurality of internal formations spatially separated from each other along one direction of the septum, the spatially separated formations lying along respective planes that extend along an other direction orthogonal to the one direction, the formations presenting a 3-D identification indicia to a viewer when the port is viewed in the one direction under radiographic imaging.

The instant invention furthermore is directed to respective methods of manufacturing the above-noted inventive septum and subcutaneously implantable port.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figure 1:
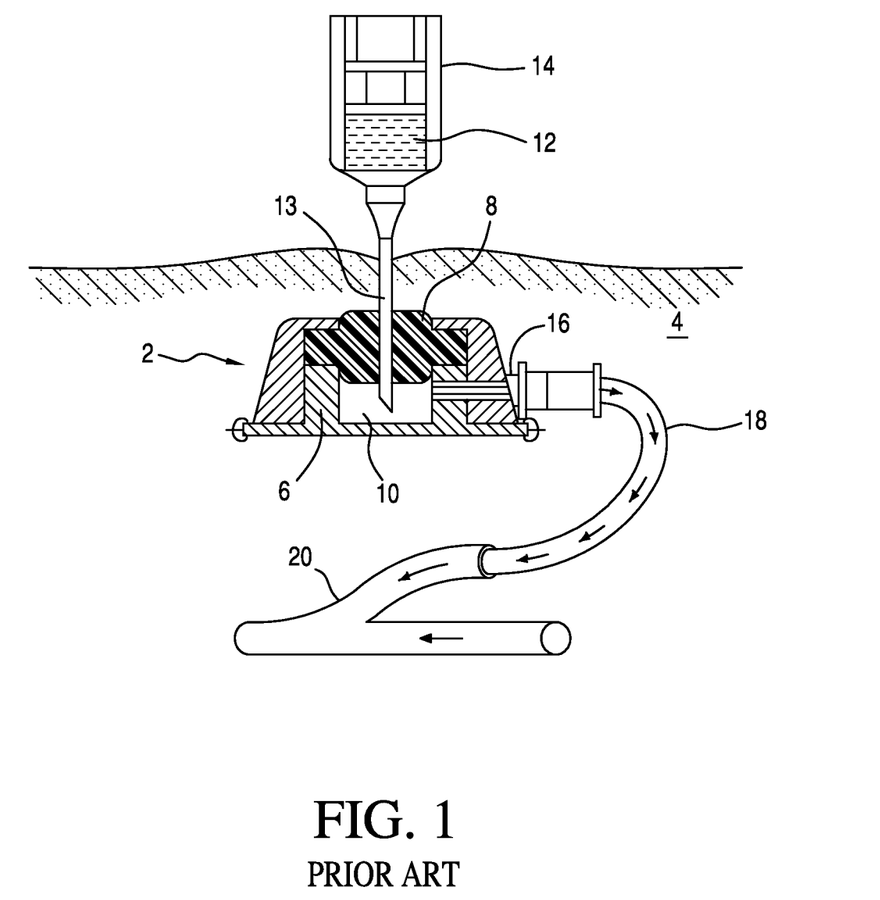
FIG. 1 is a view of a prior art portal implanted into a patient.

With reference to FIG. 1, a portal 2, such as for example that disclosed in the aforementioned U.S. Pat. No. 5,558,641, is shown to have been implanted into a patient 4. Portal 2 has a housing 6 covered by a self resealable elastomeric rubber septum 8 such that a reservoir 10 is formed in housing 6 for accepting a liquid medicament 12 from a syringe or an injection pump 14. An outlet 16 at housing 6 is connected to a catheter 18, which routes the liquid medicament from reservoir 10 to a vein 20 of patient 4.

Given that the portal is subcutaneously implanted in the patient, to fill or replenish the medicament in reservoir 10, the user has to locate the portal, and specifically septum 8 so that septum 8 may be pierced by needle 13 for inputting the liquid medicament to reservoir 10. One method of locating the portal is by palpation. To enable a user to feel the portal, tactile protrusions are provided at the top surface of the septum. However, palpation oftentimes does not accurately determine the location of the portal. Moreover, having protrusions at the septum of the portal may in practice adversely affect the piercing of the septum since the top surface of the septum is not smooth.

Another method by which the location of the portal within the patient may be ascertained is by radiographic imaging using x-ray or computer tomography. For radiographic imaging, the prior art portals have etched at their housings markings that appear under x-ray or computer tomography. However, such etching or markings at the housing, although may identify the location of the portal, do not provide in a simple and straight forward manner the accurate location of the septum where the needle has to be inserted. Moreover, the portal may move or shift within the patient, so that the location of the septum of the portal may not be readily determined at all times.

Figure 2:
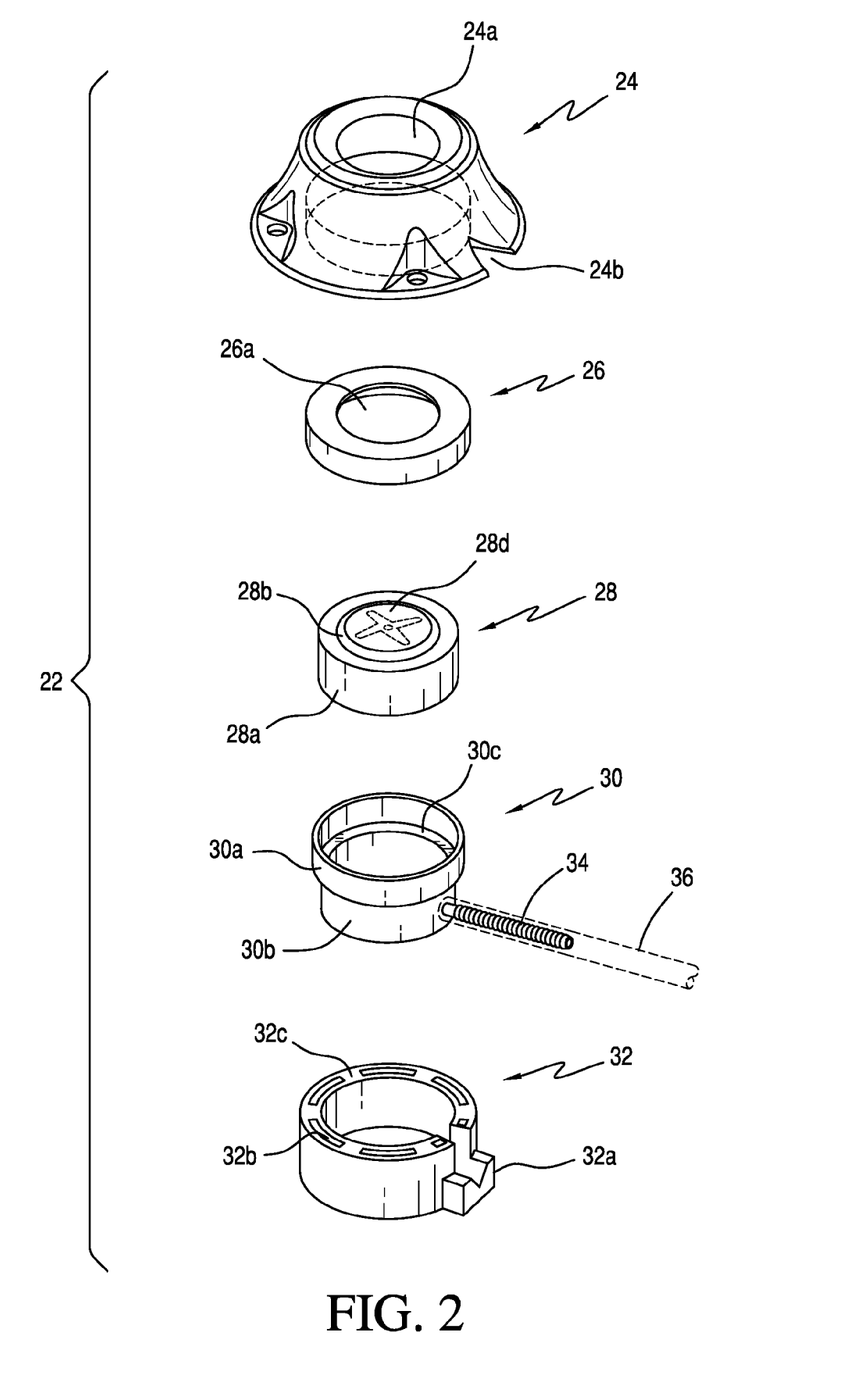
FIG. 2 is a disassembled view of the subcutaneous implantable portal of the instant invention.

With reference to FIG. 2, a disassembled view of the various components or elements of the portal of the instant invention is shown. In particular, portal 22 includes a housing 24, a cap 26, a septum 28, a reservoir body 30 and a housing base 32. Reservoir body 30 is cup-shaped and is shown to have an upper portion 30a and a lower portion 30b, which includes the base of the reservoir body 30. A shoulder 30c joins upper portion 30a to lower portion 30b. An outlet 34 extends from lower portion 30b of reservoir body 30. A conduit or catheter 36, in phantom line, is connected to outlet 34 for transporting fluid stored in reservoir body 30 to a selected location within a patient, when portal 22 is implanted subcutaneously in the patient.

Fitted to the upper portion 30a of reservoir body 30, with shoulder 30c providing a rest stop therefor, is a septum 28. As shown, septum 28 is a one piece integral unitary component that in fact may be made of different layers in multiple steps from a silicone gum stock or LIM (liquid injection molding) material, for example. Septum 28 is fabricated to have a thickness and a cross-section that enable at least the lower portion of it to be form fitted to upper portion 30a of reservoir body 30. Septum 28 is molded to have a flat bottom surface 28a and a top surface 28b defining a main structure 28c therebetween. Septum 28 is further shown to have an exemplar identification indicia, in the form of an identification logo or configuration 40, when view from atop its top surface 28b.

Figure 3A:
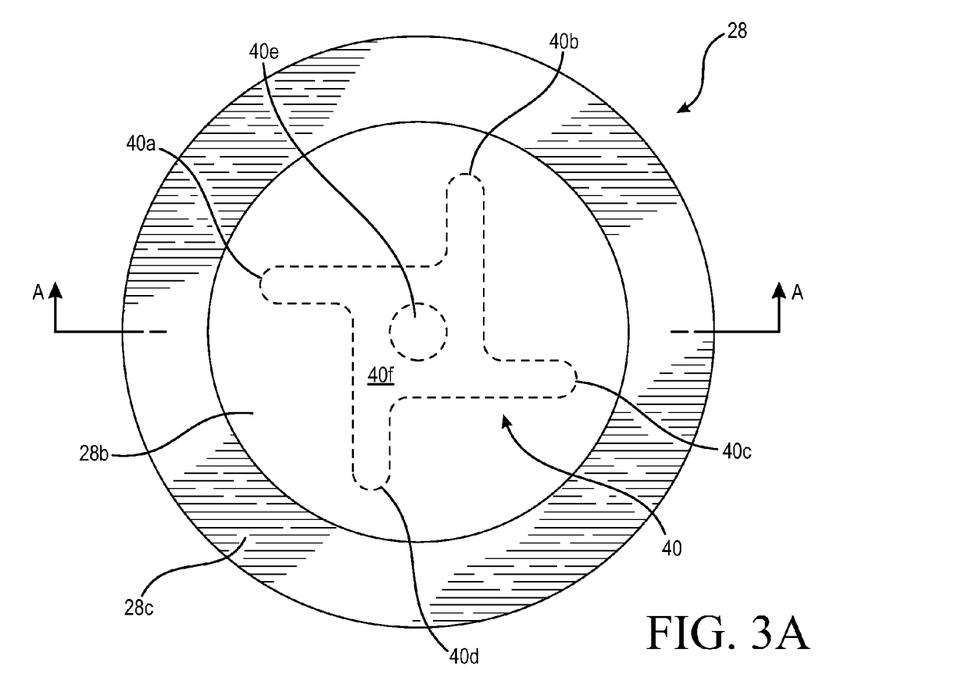
FIG. 3A shows the top view of an inventive septum having an exemplar 3-D identification logo made up of formations embedded in the septum.
Figure 3B:
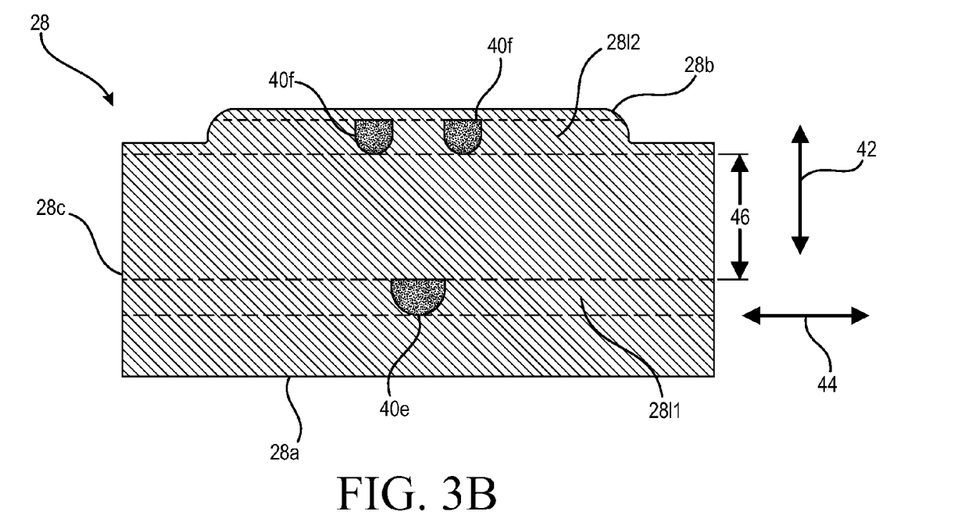
FIG. 3B is a cross-sectional view of the FIG. 3A septum.

With reference to FIGS. 3A and 3B, identification logo 40 is viewed from top surface 28b along one direction looking into the paper. For ease of discussion, this one direction may be the vertical axis, represented by the bi-directional arrows 42, of the cross-sectional view of the septum in FIG. 3B. For reference purpose, an other direction that is orthogonal to the one direction, i.e., vertical axis 42, may be the horizontal axis of the septum, per shown by bidirectional arrows 44 in FIG. 3B. Logo 40 is shown to have four extensions or fingers 40a-40d joined together to form a formation 40f with the shown given configuration. Centrally located within logo 40 is a circle formation 40e. Although shown in the plan view of FIG. 3A to be a four-fingered formation with an opening, in actuality, when viewed under radiographic imaging, for example x-ray or computer tomography, a 3-D (three dimensional) image is presented to the viewer, as formations 40e and 40f are located at a spatial distance from each other along axis 42 within septum 38, per shown by the cross-sectional view of FIG. 3B.

For the exemplar septum 28 of FIGS. 3A and 3B, formation 40e results from an impression formed in a layer 2811, while formation 40f is effected by an impression formed in a layer 2812 in the main body structure 28c of septum 28. Given that layers 2811 and 2812 are separated by a distance 46, under radiographic imaging and viewed from top surface 28b of septum 28, which is a part of portal 22, logo 40 is seen as a 3-D identification indicia, or identifier of the portal. That logo 40 is seen as a 3-D indicia from the top of the septum is advantageous since the clinician viewer can then use the 3-D identification indicia as a 3-D marker to guide him in inserting the needle into the portal, without having to guess or estimate the location of the septum or the area of the septum whereto the needle needs to be inserted, and also without having to rotate the sensor of the radiographic machine relative to the port in order to obtain a 3-D image as is conventionally done. As shown in FIG. 3B, layers 2811 and 2812 onto which formations 40e and 40f, respectively, are impressed lie along respective in parallel planes that extend along the other direction, i.e., the horizontal axis 44, that is orthogonal to the one direction, i.e., the vertical axis 42, along which the 3-D identification indicia or marker of the inventive septum may be viewed.

Figure 3C:
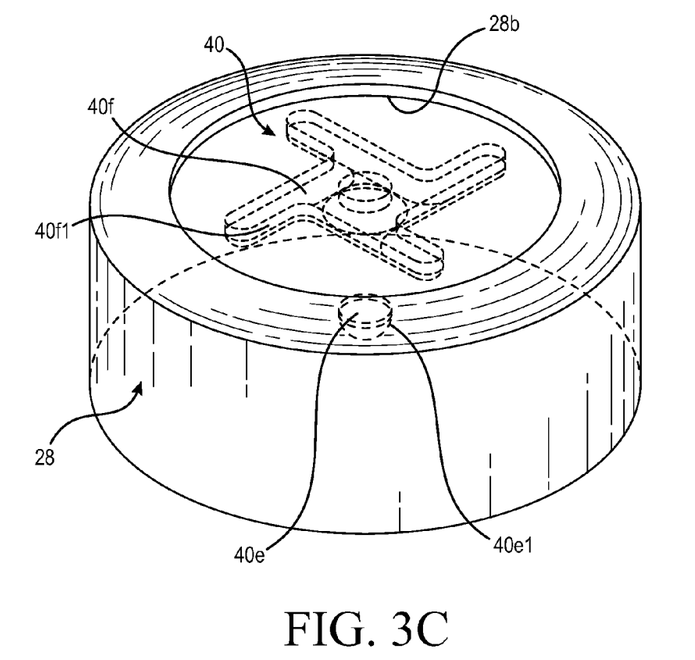
FIG. 3C is a perspective semi-sectional view of the exemplar septum of FIG. 3A.

FIG. 3C is a semi-exposed perspective view of the septum shown in FIGS. 3A and 3B. As shown, formation 40f is effected by the impression 40f1 formed at layer 2812, shown in FIG. 3B, while formation 40e is effected by the impression 40e1 formed at layer 2811. Together with FIG. 3B, it can be seen that formations 40e and 40f do not overlap, when viewed from top surface 28b of the septum along the one direction. In other words, even though formation 40f superposes over formation 40e, the configuration of formation 40f is such that it does not block the viewing of formation 40e when the septum is viewed in the direction along axis 42 under radiographic imaging. This non-overlapping of the layered formations enhances the visibility of the 3-D image of logo 40 under radiographic imaging. Although formations 40f and 40e are shown in FIG. 3B to be separated by distance 46, it should be appreciated that the spatial distance between those formations embedded within septum 28 can be varied, for example by empirical studies, to obtain an optimal 3-D image.

As the silicone material from which septum 28 is made is transparent, septum 28 itself is substantially transparent. To enhance the visibility of the 3-D indicia marker image when the portal has been implanted subcutaneously in a patient, the impressions in the layers that effect the formations, for example the respective impressions in layers 2811 and 2812 for the exemplar septum 28 of FIGS. 3A and 3B, are filled with a radiopaque material such as barium sulfate (BaSO4), or some other similar radiopaque material viewable under radiographic imaging. With the impressions in septum 28 filled with the radiopaque material, the formations can readily be viewed as a 3-D image along the vertical direction as discussed above under radiographic imaging, for example either x-ray or computer tomography (CT) imaging.

Figure 4:
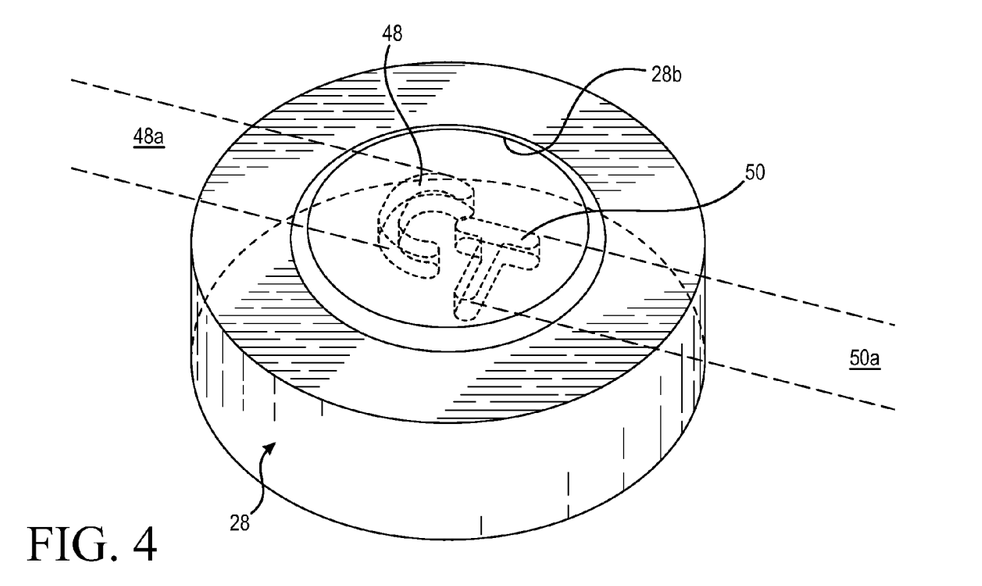
FIG. 4 is a perspective view of another exemplar septum having embedded therein alphanumeric characters at different layers of the septum.

To convey at least one property or characteristic of the portal to which septum 28 is fitted, the formations embedded in the inventive septum may be formed or configured as letter(s), character(s), number(s), combinations thereof, or some other identifying indicia. One such example is shown in FIG. 4. There, the letters "C" and "T" are formations configured from impressions 48 and 50, respectively, formed at different layers, at different depths, within the structure of septum 28. For ease of discussion, impressions 48 and 50 may also be referred to as formations 48 and 50. The layer 48a (shown by double dotted lines) onto which formation 48 is impressed lies along a plane that extends along the horizontal direction, i.e., axis 44 in FIG. 3B, that is higher than the plane along which the layer 50a where formation 50 is impressed within the septum. For the exemplar septum of FIG. 4, the formations "C" and "T" are positioned beside each other, although at the different layers 48a and 50a within the septum.

Formations 48 and 50 each are filled with a radiographic material such as barium sulfate to enhance the visibility of those formations under radiographic imaging. Even though it may appear that there is a slight overlap between formations "C" and "T" in the perspective view of FIG. 4, in actuality when septum 28 is viewed from top surface 28b, formations "C" and "T" do not overlap. That formations 48 and 50 lie on in parallel planes at different depths within septum 28 enables the viewer to see those formations as a 3-D alphanumeric identification indicia that may also act as a 3-D marker to pinpoint the location at the septum where he may insert the needle. The use of the alphanumeric formations "C" and "T" may identify for the viewer that the portal to which the septum is fitted is a power injection portal.

Figure 5A:
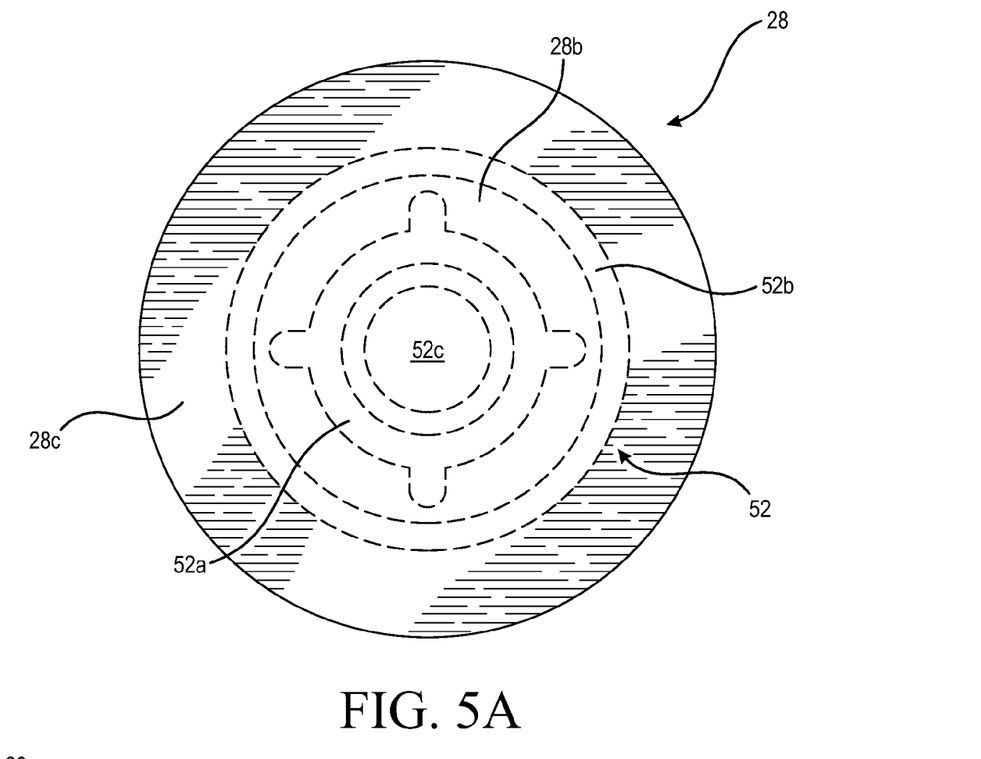
FIGS. 5A and 5B are the top and cross-sectional views, respectively, of yet another exemplar septum of the instant invention.
Figure 5B:
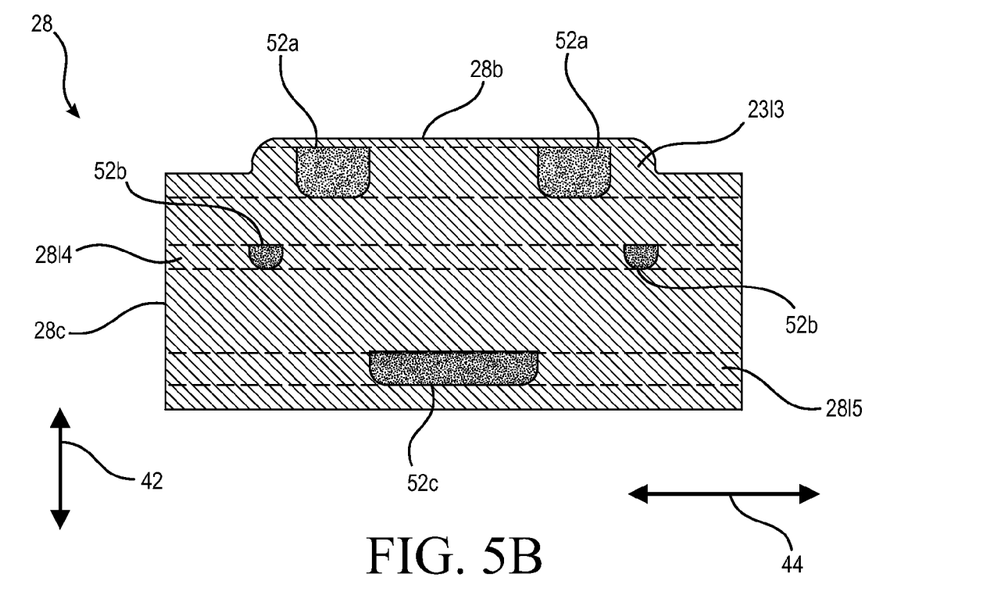

Although septums with two formations at different layers are discussed with reference to FIGS. 3A-3C and FIG. 4, in practice, the septum of the instant invention may have a plurality of formations at different layers that are spatially separated along the vertical axis within the structure of the septum. An exemplar septum with an identification logo represented by a plurality of layers, in this instance three, is shown in FIGS. 5A and 5B. There, an identification logo 52, shown in the plan view of FIG. 5A, is made up of a first formation 52a, a second formation 52b and a third formation 52c. As shown in the cross-sectional view of FIG. 5B, formation 52a is configured from an impression formed in layer 2813, formation 52b is configured from an impression formed in layer 2814, and formation 52c is configured from an impression formed in layer 2815. The different layers, along with their respective impressions, may be formed one on top of the other during the molding process with the radiographic material filling each of the impressions before additional layers are added. As shown, formations 52a, 52b and 52c are in alignment along the one direction, vertical axis 42, such that they do not overlap each other, when viewed from top surface 28b along the one direction. Also, the layers 2813, 2814 and 2815 where the formations 52a, 52b and 52c, respectively, lie are positioned in parallel relative to each other along the other direction, horizontal axis 44, orthogonal to the one direction. Same as in the earlier embodiments, when the septum embodiment shown in FIGS. 5A and 5B is viewed under radiographic imaging from top surface 28b, a 3-D identification indicia and/or marker is seen by the viewer. As noted above, there may be instances where more than three spatially spaced formations may be embedded into the septum to provide the 3-D identification indicia/marker.

Figure 6:
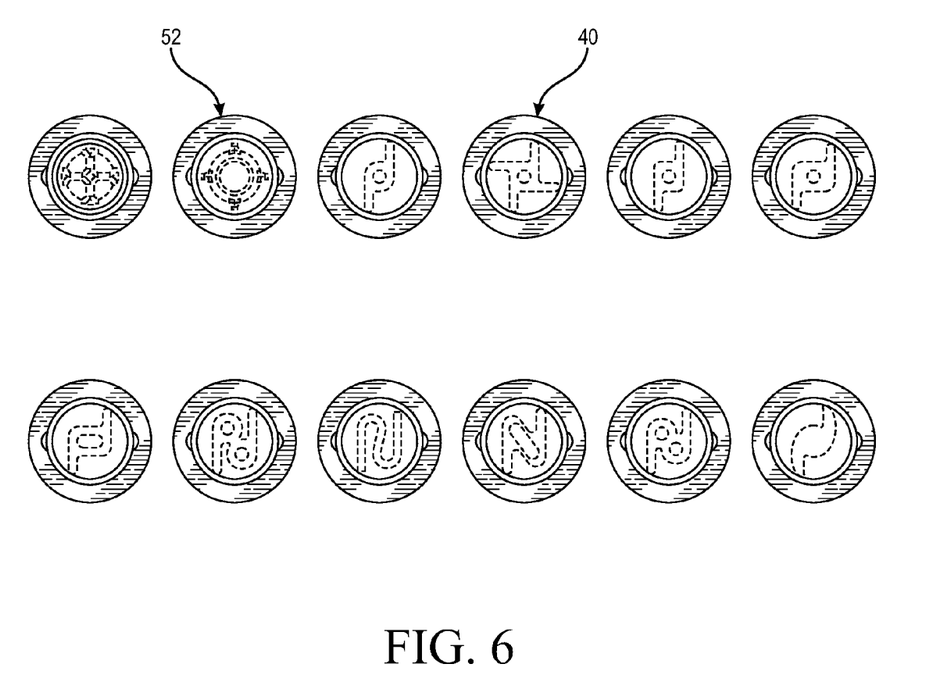
FIG. 6 shows illustrations of exemplar septums of the instant invention having different 3-D identification logos embedded therein.

FIG. 6 shows in plan view a number of the septums of the instant invention having different identification logos or configurations formed therein. Two of those logos, namely 40 and 52, are the logo configurations shown in FIGS. 3A-3C and FIGS. 5A-5B. All of the logo configurations shown in the septums of FIG. 6 have formations that are embedded in different layers in the septum to provide a 3-D image usable as a 3-D identification indicia and/or a 3-D needle insertion marker.

Returning to FIG. 2, once septum 28 is fitted to the upper portion 30a of reservoir body 30, to hold septum 28 in place, a cap 26 is friction fitted over top portion 30a of reservoir body 30. For the exemplar portal embodiment of FIG. 2, both cap 26 and reservoir body 30 are made from titanium, or some other inert metal acceptable for implantation to a patient. An opening 26a at cap 26 exposes the indicia logo marker embedded in septum 28. The assembled reservoir housing—made up of reservoir body 30, septum 28 and cap 26—is then be placed in housing base 32. Housing base 32 is in the form of a collar with its inside diameter having a dimension sufficient to receive reservoir body 30, and a notched support 32a at a side thereof for accepting outlet 34. Housing 24 is then positioned over housing base 32 to envelop the assembled reservoir housing. A slot 24b at the lower portion of housing 24 provides accommodation for outlet 34 of reservoir body 30 that extends out of housing base 32 at support 32a. A top opening 24a at housing 24 exposes the top surface of septum 28, and therefore marking 28d embedded therein. To prevent separation, housing 24 and housing base 32 are ultrasound welded, possibly at the locations defined by the grooves 32b at the lip 32c of housing base 32. To save weight and cost, housing 24 and housing base 32 may be made from conventional medical plastics material.

Figure 7A:
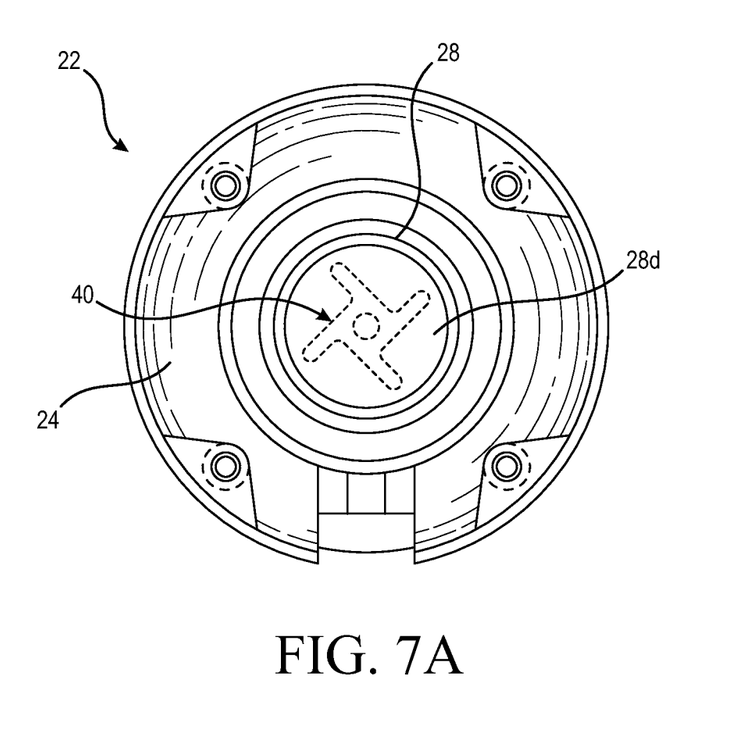
FIG. 7A is a plan view of the portal of the instant invention assembled with the exemplar septum of FIGS. 3A-3C.
Figure 7B:
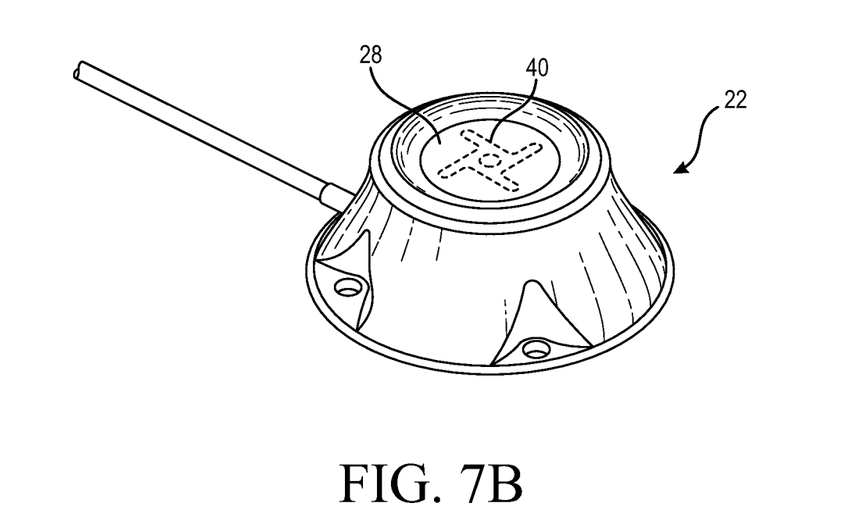
FIG. 7B is a perspective view of the portal of FIG. 7A.

A plan view of the assembled portal 22 with the 3-D identification logo marker of FIGS. 3A-3C is shown in FIG. 7A. A perspective view of the assembled exemplar portal of FIG. 2 is shown in FIG. 7B.

Inasmuch as the present invention is subject to many variations, modifications and changes in detail, it is intended that all matter described throughout this specification and shown in the accompanying drawings be interpreted as illustrative only and not in a limiting sense. For example, instead of a single reservoir portal, the present invention is also adapted to include dual reservoir ports such as that disclosed in the above noted U.S. Pat. No. 5,743,873. Further, even though the radiopaque material filled identification indicia is discussed above as viewable by x-ray and computer tomography imaging, given the multiple formations are formed as impressions on different layers of the septum, the respective depths or configurations of the formations enable the formations to reflect sound waves, so that the portal of the instant invention, per its inventive septum, in addition to being viewable under x-ray and computer tomography imaging, is also viewable under ultrasound imaging.

The invention claimed is:

1. A self resealable septum, comprising: an elastomeric structure having at least two impressions embedded therein, the impressions being spatially separated from each other along one direction of the structure, each of the impressions configured to have a formation, formations resulting from the impressions spatially separated from each other along the one direction, each of the formations not blocked when viewed along the one direction, the formations together presenting a 3-D identification indicia to a viewer when the structure is viewed along the one direction under radiographic imaging.

2. Septum of claim 1, wherein the formations in the structure each lie along a corresponding plane that extends along an other direction orthogonal to the one direction so that the formations lie along respective planes, the formations do not overlap each other along the one direction when viewed from atop of the structure.

3. Septum of claim 1, wherein the formations are positioned in the septum such that when the septum is viewed along the one direction, the 3-D identification indicia presents a marker at the structure to guide the insertion of a needle thereto.

4. Septum of claim 1, wherein each of the impressions is filled with a radiopaque material visible under radiographic imaging including computer tomography and/or x-ray imaging.

5. Septum of claim 4, wherein the radiopaque material comprises barium sulfate (BaSO4), and wherein the elastic structure is made from silicone.

6. Septum of claim 1, wherein the septum is fitted to an opening of a subcutaneous implantable port; and wherein the identification indicia identifies the port as a power injection port.

7. Septum of claim 1, wherein the structure comprises a plurality of elastomeric layers, each of the formations formed on a corresponding layer and filled with a radiopaque material, the layers integrally bonded to each other so that the structure is an integral one piece unitary component with the identification indicia formed by the spatially separated layers of formations embedded in the structure.

8. A subcutaneously implantable port, comprising:
a housing having an opening and an outlet; and
a resealable elastomeric septum fitted to the opening of the housing to define a fluid reservoir inside the housing, the septum having a plurality of internal formations spatially separated from each other along one direction of the septum, the spatially separated formations lying along respective planes that extend along an other direction orthogonal to the one direction, the formations presenting a 3-D identification indicia to a viewer when the port is viewed in the one direction under radiographic imaging.

9. Port of claim 8, wherein the formations are formed as impressions filled with a radiopaque material visible under radiographic imaging including computer tomography and/or x-ray imaging for providing the 3-D identification indicia to the viewer along the one direction.

10. Port of claim 9, wherein the radiopaque material comprises barium sulfate (BaSO4).

11. Port of claim 8, wherein the 3-D identification indicia presents a marker at the septum to guide the insertion of a needle into the fluid reservoir through the septum.

12. Port of claim 8, wherein the 3-D identification indicia identifies the port as a power injection port.

13. Port of claim 8, wherein the septum comprises a plurality of elastomeric layers, each of the formations formed on a corresponding layer and filled with a radiopaque material, the layers integrally bonded to each other so that the septum is an integral one piece unitary component with the identification indicia formed by the spatially separated layers of formations positioned in the septum, the unitary component being silicone.

14. Port of claim 8, wherein the plurality of formations each are filled with a radiopaque material, the formations do not overlap when viewed from atop of the septum along the one direction.

15. Septum of claim 1, wherein one of the formations is a C and another of the formations is a T.

16. Port of claim 8, wherein one of the formations is a C and another of the formations is a T.

17. A septum, comprising: an elastomeric structure having a top surface and a plurality of impressions embedded within the elastomeric structure, the impressions being spatially separated from each other along one direction orthogonal to the top surface of the structure, each of the impressions formed in a corresponding layer of the structure along an other direction orthogonal to the one direction, the impressions configured as respective formations spatially separated from each other along the one direction.

18. Septum of claim 17, wherein the impressions do not overlap each other along the one direction, the impressions together presenting a 3-D indicia when the structure is viewed under radiographic imaging from the one direction.

19. Septum of claim 17, wherein each of the impressions is filled with a radiopaque material visible under radiographic imaging including computer tomography and/or x-ray imaging.

20. Septum of claim 4, wherein the radiopaque material comprises barium sulfate (BaSO4), and wherein the elastic structure is made from silicone.

* * * * *